United States Patent
Houben et al.

(10) Patent No.: US 7,203,551 B2
(45) Date of Patent: Apr. 10, 2007

(54) IMPLANTABLE LEAD-BASED SENSOR POWERED BY PIEZOELECTRIC TRANSFORMER

(75) Inventors: Richard P. M. Houben, Lanaken (BE); Mark A. Christopherson, Shoreview, MN (US); Adrianus P. Donders, Andover, MN (US); Robert Leinders, Limbricht (NL); Curtis D. Deno, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 630 days.

(21) Appl. No.: 10/424,584

(22) Filed: Apr. 25, 2003

(65) Prior Publication Data

US 2004/0215279 A1    Oct. 28, 2004

(51) Int. Cl.
*A61N 1/00* (2006.01)
*H01L 41/07* (2006.01)

(52) U.S. Cl. .................. 607/116; 607/115; 310/366

(58) Field of Classification Search .............. 607/16, 607/19, 115–116, 35, 119, 122; 310/366
See application file for complete search history.

(56) References Cited

U.S. PATENT DOCUMENTS

| | | | | |
|---|---|---|---|---|
| 3,421,512 A | * | 1/1969 | Frasier | 607/35 |
| 4,023,562 A | | 5/1977 | Hynecek et al. | 128/2.05 E |
| 4,109,644 A | * | 8/1978 | Kojima | 600/437 |
| 4,432,372 A | | 2/1984 | Monroe | 128/675 |
| 4,690,143 A | * | 9/1987 | Schroeppel | 607/5 |
| 4,846,178 A | * | 7/1989 | Fuxue et al. | 607/2 |
| 5,484,404 A | * | 1/1996 | Schulman et al. | 604/66 |
| 5,620,479 A | * | 4/1997 | Diederich | 601/3 |
| 5,807,258 A | * | 9/1998 | Cimochowski et al. | 600/454 |
| 6,707,235 B1 | * | 3/2004 | Brebøl | 310/369 |
| 2001/0026111 A1 | * | 10/2001 | Doron et al. | 310/322 |
| 2002/0183800 A1 | | 12/2002 | Schmidt et al. | 607/32 |
| 2004/0174098 A1 | * | 9/2004 | Hsu et al. | 310/366 |
| 2004/0215243 A1 | * | 10/2004 | Houben et al. | 607/5 |

FOREIGN PATENT DOCUMENTS

WO    WO 01/09640 A1    2/2001

* cited by examiner

*Primary Examiner*—Robert E. Pezzuto
*Assistant Examiner*—Jessica L. Reidel
(74) *Attorney, Agent, or Firm*—Michael C Soldner; Girma Wolde-Michael

(57) ABSTRACT

In general, the invention is directed to an IMD having a piezoelectric transformer to power a lead-based sensor. The IMD powers the piezoelectric transformer with a low amplitude signal. The piezoelectric transformer serves to convert the voltage level of the low amplitude signal to a higher voltage level to drive the sensor produced by a battery in the IMD to voltage levels appropriate for IMD operation. A piezoelectric transformer offers small size and low profile, as well as operational efficiency, and permits the IMD to transmit a low amplitude signal to a remote sensor deployed within an implantable lead. In addition, the piezoelectric transformer provides electrical isolation that reduces electromagnetic interference among different sensors.

26 Claims, 2 Drawing Sheets

IMPLANTABLE LEAD-BASED SENSOR POWERED BY PIEZOELECTRIC TRANSFORMER

FIELD OF THE INVENTION

The invention relates to implantable medical devices and, more particularly, to implantable medical devices that include lead-based sensors.

BACKGROUND OF THE INVENTION

Implantable medical devices (IMDs), such as implantable cardiac pacemakers, pacemaker-cardioverter-defibrillators, neurostimulators, gastric stimulators, drug pumps, loop recorders, and the like, generally make use of battery power to support the output and functionality of such devices. An IMD is typically designed for use over a period of years, and therefore power efficiency and associated battery consumption is a significant concern.

Some IMDs receive signals from sensors carried by implantable leads. A sensor may be responsive to a sensed condition in the body, such as electrical activity, blood pressure, blood chemistry or a mechanical property. Sensors responsive to sensed conditions may detect or measure a quantity of clinical significance. Some sensors require power to support sensor operation. Examples of powered sensors include ultrasonic sensors, infrared sensors, cameras and the like.

Conventional powered sensors receive power from a battery, which may be positioned with an IMD housing. An IMD delivers power to a sensor by way of a lead that includes a conductor. In general, powered sensors contribute to power consumption and battery drain, and can compromise IMD longevity.

BRIEF SUMMARY OF THE INVENTION

In general, the invention is directed to an IMD having a piezoelectric transformer to power a lead-based sensor. The IMD powers the piezoelectric transformer with a low amplitude signal. The piezoelectric transformer-serves to convert the voltage level of the low amplitude signal to a higher voltage level to drive the sensor. produced by a battery in the IMD to voltage levels appropriate for IMD operation. A piezoelectric transformer offers small size and low profile, as well as operational efficiency, and permits the IMD to transmit a low amplitude signal to a remote sensor deployed within an implantable lead. In addition, the piezoelectric transformer provides electrical isolation that reduces electromagnetic interference among different sensors.

In general, the piezoelectric transformer includes two or more piezoelectric resonators. The piezoelectric resonators are mechanically coupled to one another, but electrically insulated. An input circuit, coupled to a battery in the IMD, generates an input signal near a resonant frequency of an input resonator, and transmits the signal along the length of the lead to the piezoelectric transformer via an electrical conductor.

In some embodiments, the input circuit may be a pulse frequency modulation circuit. The input resonator receives the input signal, and generates mechanical vibration due to the piezoelectric converse effect. An output resonator transduces the mechanical vibration to generate an output signal at a second voltage level, due to the piezoelectric direct effect. The output resonator applies the output signal to a sensor, either directly or via an output stage circuit, thereby powering the sensor.

In this manner, the IMD uses the output signal from the piezoelectric transformer to support sensor operation. The IMD may be, for example, an implantable cardiac pacemaker, pacemaker-cardioverter-defibrillator, a neurostimulator, a drug pump, a loop recorder, or the like. The IMD applies the output signal generated by the piezoelectric transformer to power a variety of sensors including ultrasonic sensors, infrared sensors, cameras and the like.

In one embodiment, the invention provides an implantable medical device comprising a battery to deliver a first voltage, a piezoelectric transformer to convert the first voltage to a second voltage greater than the first voltage, and a sensor powered by the second voltage.

In another embodiment, the invention provides an implantable medical device comprising a battery to deliver a first voltage, an input circuit to generate an input signal derived from the first voltage, a piezoelectric transformer to convert the first voltage to a second voltage greater than the first voltage, wherein the piezoelectric transformer includes a first resonator that generates mechanical vibration in response to the input signal, and a second resonator that generates an output signal in response to the mechanical vibration, a sensor powered by the second voltage, and an implantable lead, wherein the sensor is disposed within the lead.

In a further embodiment, the invention provides an implantable medical lead comprising a lead body, a piezoelectric transformer within the lead body, and a sensor within the lead body and electrically coupled to the piezoelectric transformer, wherein the piezoelectric transformer includes a first resonator that generates mechanical vibration in response to an input signal, and a second resonator that generates an output signal in response to the mechanical vibration, and the sensor is powered by the second voltage.

In another embodiment, the invention provides a method comprising converting a first voltage to a second voltage with a piezoelectric transformer, wherein the second voltage is greater than the first voltage, and applying the second voltage to a sensor within an implantable medical device.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
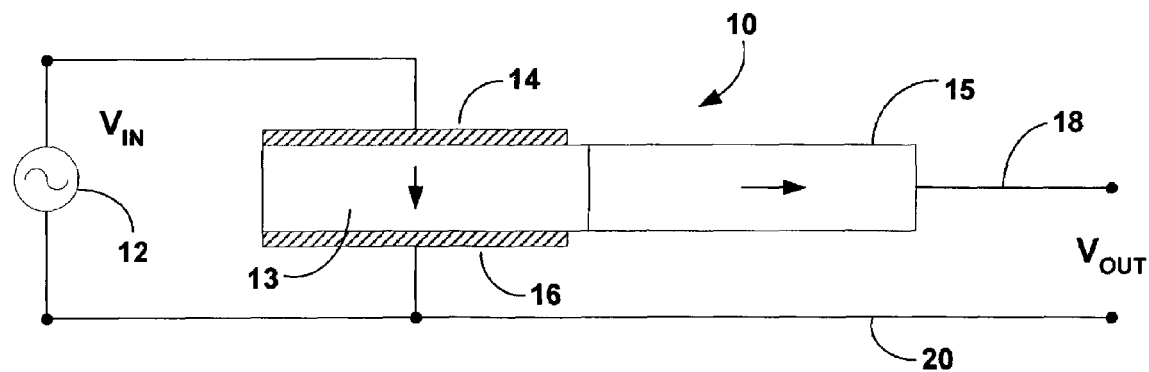
FIG. 1 is a schematic view illustrating a piezoelectric transformer.

FIG. 1 is a schematic view illustrating a piezoelectric transformer 10. An input circuit 12 drives piezoelectric transformer 10 with an input signal $V_{IN}$ having a frequency matched approximately to the resonant frequency of piezoelectric transformer 10. Piezoelectric transformer 10 includes a first (input) resonator 13 sandwiched between electrodes 14, 16, and a second (output) resonator 15 having an output 18 that generates an output signal $V_{OUT}$. A common ground 20 serves as reference for input signal $V_{IN}$ and output signal $V_{OUT}$.

As described herein, piezoelectric transformer 10 serves to convert a first voltage to a second voltage higher than the first voltage within an IMD. The first voltage is generated with power delivered by a battery within the IMD. The second voltage ($V_{OUT}$) is applied to support operation of a lead-based sensor, i.e., a sensor carried by an implantable lead associated with the IMD. Examples of powered sensors suitable for use with piezoelectric transformer 10 include ultrasonic sensors, infrared sensors, cameras and the like.

Piezoelectric transformer 10 offers a small size and low profile, facilitating placement of the piezoelectric transformer within an implantable lead. In addition, piezoelectric transformer 10 offers good power efficiency. For example, some commercially available piezoelectric transformers are known to offer 80 to 90 percent power efficiency. In addition, piezoelectric transformer 10 provides electrical isolation that reduces electromagnetic interference among different sensors.

In operation, the first and second resonators 13, 15 of piezoelectric transformer 10 are mechanically coupled to one another, but electrically insulated from one another. Input circuit 12, coupled to a battery (not shown in FIG. 1), generates the input signal $V_{IN}$ near a resonant frequency of the input resonator. In response, the input resonator 13 generates mechanical vibration, due to the piezoelectric converse effect. The output resonator 15 transduces the mechanical vibration to generate output signal $V_{OUT}$ at a second voltage level, due to the piezoelectric direct effect.

Figure 2:
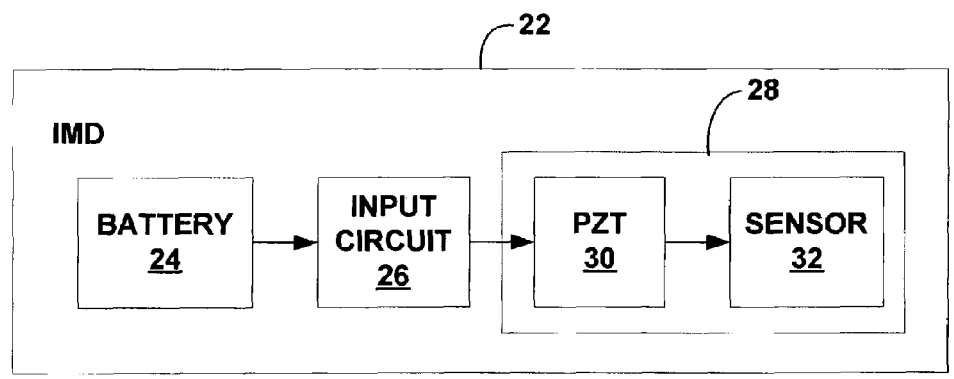
FIG. 2 is a block diagram illustrating an implantable medical device incorporating a piezoelectric transformer to power a lead-based sensor.

FIG. 2 is a block diagram illustrating an IMD 22 incorporating a piezoelectric transformer (PZT). As shown in FIG. 2, IMD 22 includes a battery 24 that provides power to an input circuit 26. The power delivered by battery 24 has a first voltage level. An implantable lead 28 carries a PZT 30 and a powered sensor 32. Input circuit 26 generates an input signal to drive PZT 30 at or near a resonant frequency of the PZT. PZT 30 receives the input signal via electrical conductors within the implantable lead. In response, PZT 30 generates an output signal at a second voltage greater than the first voltage.

PZT 30 applies the second voltage to power sensor 32, either directly or via an output circuit. Sensor 32 uses the power provided by PZT 30 for operation. For example, if sensor 32 is an ultrasonic sensor, it uses the power to emit ultrasonic energy. Sensor 32 then captures reflections of the ultrasonic energy to sense physiological parameters such as blood flow, blood pressure, valve closure in the case of a cardiac device, or the like.

The first voltage provided by input circuit 26 may be less than or equal to approximately 50 millivolts. More particularly, the first voltage may be in the range of approximately 10 to 50 millivolts. Similarly, the input signal generated by input circuit 26 may generate an ac signal with a peak amplitude on the order of 10 to 50 millivolts. The second voltage delivered by PZT 30, however, may be in excess of approximately 3 volts. For example, a typically commercially available piezoelectric transformer having a transformation ratio of 65 will transform a 50 millivolt input signal to a level of approximately 3.25 volts. The resonance frequency of a typical piezoelectric transformer may in the range of approximately 50 kHz to 100 kHz. Hence, the first voltage delivered by battery 24 may be less than fifty percent of the second voltage and, in many, cases less than twenty percent of the second voltage.

The second voltage may be provided-directly from PZT 30. Alternatively, the second voltage may be generated by an output circuit. In some embodiments, PZT 30 may be used to power multiple sensors within an implantable lead. For example, the lead may incorporated multiple sensors of a common type, of different types of sensors, each of which can be powered by PZT 30.

Figure 3:
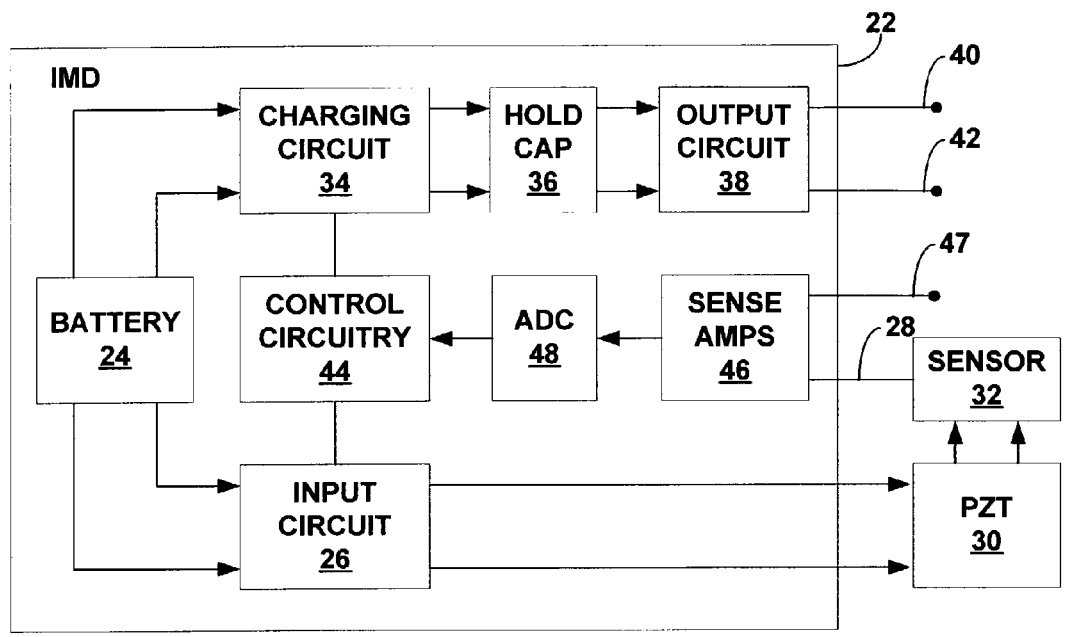
FIG. 3 is a block diagram illustrating the implantable medical device of FIG. 2 in greater detail.

FIG. 3 is a block diagram illustrating IMD 22 incorporating a lead-based sensor powered by a piezoelectric transformer. In the example of FIG. 3, IMD 22 is depicted as an implanted cardioverter-defibrillator (ICD) for purposes of illustration. However, other types of IMDs may take advantage of a piezoelectric transformer to power a lead-based sensor. For example, in other embodiments, IMD 22 may be an implantable cardiac pacemaker, neurostimulator, a gastric stimulator, a drug pump, a loop recorder, or the like.

As shown in FIG. 3, IMD 22 includes battery 24, input circuit 26, PZT 30, and sensor 32. In addition, to support delivery of cardioversion or defibrillation shocks, IMD 22 includes a charging circuit 34 coupled to battery 24, a hold capacitor 36 charged by charging circuit 34, and an output circuit 38 that drives one or more stimulation electrodes deployed within the heart via implantable leads 40, 42 to deliver shocks. Control circuitry 44 controls charging circuit 34 and output circuit 38 to deliver cardioversion and/or defibrillation shocks via stimulation leads 40, 42. As an example, lead 40 may be carried by a right atrial lead and lead 42 may be carried by a right ventricular lead. Leads 40, 42 may include both stimulation electrodes and sense electrodes.

One or more sense amplifiers 46 receive physiological signals from powered sensor 32, deployed on lead 28. In addition, sense amplifiers 46 may receive other physiological signals via other leads, such as lead 47. For example, sense amplifiers 46 may process cardiac signals obtained from one or more sense electrodes deployed on lead 47. The sense electrodes and powered sensor 32 are deployed within the heart via implantable leads 47, 28, respectively. For example, one or more sense electrodes may be carried by a right atrial lead and one or more sense electrodes may be carried by a right ventricular lead. The powered sensor may be carried by an atrial or ventricular lead.

An analog-to-digital converter (ADC) 48 converts the sensed physiological signals to digital values for processing and analysis by control circuitry 44, which may include a microprocessor, digital signal processor, ASIC, FPGA, or other equivalent logic circuitry. Control circuitry 44 may be respond to the rate, timing, amplitude, or morphology of the physiological signals in controlling charging circuit 34 and output circuit 38 to deliver cardioversion and defibrillation shocks, as well as in controlling blanking intervals for sense amplifiers 46. IMD 22 further includes a telemetry circuit (not shown) for wireless communication with an external programmer.

In operation, input circuit 26 generates an input signal having a frequency approximately matched to a resonant frequency of the input resonator of PZT 30. The input signal may have a sinusoidal waveform, and an amplitude substantially less than the operating power level required by sensor 32. In some embodiments, input circuit 26 may include closed loop feedback to detect the output voltage produced by PZT 30, and adjust the frequency or amplitude of the input signal based on the detected output voltage. In this manner, input circuit 26 causes PZT 30 a controlled, substantially constant output voltage.

PZT 30 offers a small size that permits the PZT to be placed within an implantable lead to powered sensor 32 carried by the lead. Advantageously, PZT 30 also may enable the realization of a sensor 32 that is resistant to circuit-induced inter-channel cross-current. For example, inclusion of PZT 30 provides electrical isolation, and thereby circumvents possible current paths from sensor 32 to other sensors. Reduced interference promotes more accurate sensing on non-stimulation channels.

In addition, the use of PZT 30 can help to protect sensor 32 from electromagnetic interference. Specifically, piezoelectric elements are insensitive to electromagnetic interference. Accordingly, sensor performance is unaffected by presence of electromagnetic interference induced in the electrical conductors extending along the lead. In particular, PZT 30 may serve to better isolate sensor 32 from electrical interference caused by MRI procedures or emissions from equipment within the environment occupied by the patient.

Figure 4:
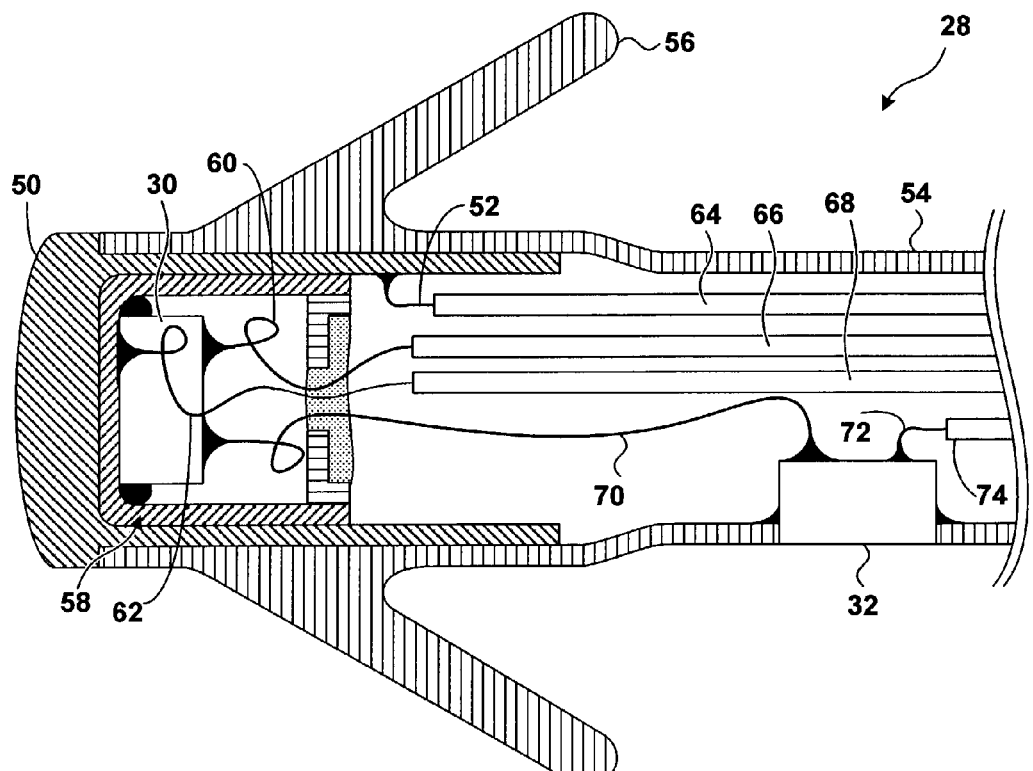
FIG. 4 is a cross-sectional side view of a distal end of an implantable medical lead incorporating a piezoelectric transform to power a lead-based sensor.

FIG. 4 is a cross-sectional side view of a distal end of an implantable lead 28 carrying a sensor 32 and a piezoelectric transformer 30 to power the sensor. As shown in FIG. 4, the distal end of lead 28 may include an electrode 50, which transmits or receives electrical signals or pacing stimuli from IMD 22 (not shown in FIG. 4) via a conductor 52. Electrode 50 is coupled to an insulating sheath 54. Tines 56 projecting from sheath 54 present a fixation mechanism that anchors the distal end of lead 28 in cardiac tissue.

PZT 30 is disposed inside the distal end of lead 14. As shown in FIG. 4, PZT 30 may be housed inside a capsule 58 and may be electrically coupled to an input circuit in IMD 22 via one or more conductors 60, 62. Conductor 60, 62 may, for example, supply a low voltage signal at approximately the resonant frequency of an input resonator in PZT 30. Conductors 52, 60, 62 may be carried within lead 28 by insulative conduits 64, 66, 68, respectively.

Sensor 32 is electrically coupled to the output-resonator of PZT 30 via conductor 70. The input resonator in PZT 30 converts the low voltage input signal transmitted by conductors 60, 62 into mechanical energy, which is then transduced by the output resonator to produce the output signal with an increased voltage. Sensor 32 receives the output signal from PZT 30 via conductor 70. In this way, PZT 30 powers sensor 32. Sensor 32 applies power from PZT 30 to detect or measure sensed conditions. In addition, sensor 32 transmits sensed signals to IMD 22 via conductor 72, housed in insulative conduit 74.

The arrangement depicted in FIG. 14 is exemplary, and the invention is not limited to the application shown. PZT 30 need not be housed in a capsule, for example, and need not be directly coupled to sensor 32. Rather, intermediate output circuitry may stand between PZT 30 and sensor 32 to shape or condition the output signal. The invention may be practiced with leads of various configurations, including leads with bipolar electrodes, leads with fixation mechanisms other than tines, and leads configured to provide steroid elution.

Many embodiments of the invention have been described. Various modifications can be made without-departing from the scope of the claims. These and other embodiments are within the scope of the following claims.

What is claimed is:

1. An implantable medical device comprising:
    a battery to deliver a first voltage derived exclusively from the battery, wherein the battery is adapted to be implanted internally relative to a patient's skin;
    a piezoelectric transformer to convert the first voltage to a second voltage greater than the first voltage;
    a sensor powered by the second voltage; and an implantable lead, wherein the sensor and the piezoelectric transformer are disposed within the implantable lead.

2. The device of claim 1, further comprising an input circuit to receive the first voltage and to drive the piezoelectric transformer with an input signal.

3. The device of claim 2, wherein the piezoelectric transformer includes a first resonator that generates mechanical vibration in response to the input signal, and a second resonator that generates an output signal in response to the mechanical vibration.

4. The device of claim 3, wherein the input signal has a frequency approximately equal to a resonant frequency of the first resonator.

5. The device of claim 1, wherein the implantable medical device comprises one of an implantable pacemaker, an implantable cardioverter-defibrillator, an implantable neurostimulator, an implantable gastric stimulator, an implantable drug pump, and an implantable loop recorder.

6. The device of claim 1, wherein the first voltage is less than fifty percent of the second voltage.

7. The device of claim 1, wherein the first voltage is less than twenty percent of the second voltage.

8. The device of claim 1, wherein the sensor includes one of an ultrasonic sensor, an infrared sensor, and a camera.

9. The device of claim 1, wherein the second voltage is greater than or equal to 3 volts.

10. The device of claim 1, wherein the first voltage is less than or equal to 50 millivolts.

11. The device of claim 1, further comprising an input circuit to drive the piezoelectric transformer with an input signal and conductors extending within the lead to electrically couple the input circuit to the piezoelectric transformer.

12. An implantable medical device comprising:
    a battery to deliver a first voltage derived exclusively from the battery wherein the battery is adapted to be implanted internally relative to a patient's skin;
    an input circuit to generate an input signal derived from the first voltage;
    a piezoelectric transformer to convert the first voltage to a second voltage greater than the first voltage, wherein the piezoelectric transformer includes a first resonator that generates mechanical vibration in response to the input signal, and a second resonator that generates an output signal in response to the mechanical vibration;
    a sensor powered by the second voltage;
    an implantable lead, wherein the sensor and the piezoelectric transformer are disposed within the lead.

13. The device of claim 12, wherein the input signal has a frequency approximately equal to a resonant frequency of the first resonator.

14. The device of claim 12, wherein the implantable medical device comprises one of an implantable pacemaker, an implantable cardioverter-defibrillator, an implantable neurostimulator, an implantable gastric stimulator, an implantable drug pump, and an implantable loop recorder.

15. The device of claim 12, wherein the first voltage is less than fifty percent of the second voltage.

16. The device of claim 12, wherein the first voltage is less than twenty percent of the second voltage.

17. The device of claim 12, wherein the sensor includes one of an ultrasonic sensor, an infrared sensor, and a camera.

18. The device of claim 12, wherein the second voltage is greater than or equal to 3 volts.

19. The device of claim 12, wherein the first voltage is less than or equal to 50 millivolts.

20. An implantable medical lead comprising:
a lead body comprising a conductor adapted to be coupled to a battery implanted internally relative to a patient's skin;
a piezoelectric transformer within the lead body; and
a sensor within the lead body and electrically coupled to the piezoelectric transformer,
wherein the piezoelectric transformer includes a first resonator that generates mechanical vibration in response to an input signal derived from a voltage delivered exclusively by the battery, and a second resonator that generates an output signal in response to the mechanical vibration, and the sensor is powered by the second voltage.

21. The device of claim 20, wherein the sensor includes one of an ultrasonic sensor, an infrared sensor, and a camera.

22. A method for use in an implanted medical device system comprising:
converting a first voltage derived exclusively from a battery implanted internally relative to a patient's skin to a second voltage with a piezoelectric transformer, wherein the second voltage is greater than the first voltage; and
applying the second voltage to a sensor within the implanted medical device system, wherein the sensor and the piezoelectric transformer are disposed within an implantable lead of the implanted medical device system.

23. The method of claim 22, wherein converting the first voltage to a second voltage includes driving a first resonator of the piezoelectric transformer with a first signal to generate mechanical vibration, and transducing the mechanical vibration with a second resonator of the piezoelectric transformer to produce a second signal with the second voltage.

24. The method of claim 22, wherein the implantable medical device comprises one of an implantable pacemaker, an implantable cardioverter-defibrillator, an implantable neurostimulator, an implantable gastric stimulator, an implantable drug pump, and an implantable loop recorder.

25. The method of claim 22, wherein the sensor includes one of an ultrasonic sensor, an infrared sensor, and a camera.

26. An implantable cardiac electrical stimulation device, comprising:
a battery to deliver a first voltage derived exclusively from the battery, wherein the battery is adapted to be implanted internally relative to a patient's skin;
an input circuit to receive the first voltage and generate an input signal;
a piezoelectric transformer to convert the first voltage to a second voltage greater than the first voltage, wherein the piezoelectric transformer includes a first resonator that generates mechanical vibration in response to the input signal, and a second resonator that generates an output signal in response to the mechanical vibration;
a sensor powered by the output signal; and
an implantable lead, wherein the sensor and the piezoelectric transformer are disposed within the lead.

* * * * *